United States Patent [19]

DeSimone

[11] 3,976,700
[45] Aug. 24, 1976

[54] PROCESS FOR PREPARING METHYL HEPTENONE

[75] Inventor: Robert S. DeSimone, Middletown, N.Y.

[73] Assignee: Rhodia, Inc., New York, N.Y.

[22] Filed: Mar. 24, 1975

[21] Appl. No.: 561,582

Related U.S. Application Data

[63] Continuation-in-part of Ser. No. 484,494, July 8, 1974, abandoned.

[52] U.S. Cl. ............................................. 260/593 R
[51] Int. Cl.² ......................................... C07C 45/00
[58] Field of Search ............................... 260/593 R

[56] References Cited
UNITED STATES PATENTS 3,002,999   10/1961   Lichtenberger et al. ......... 260/593 R
3,668,255   6/1972    Meuly et al. ..................... 260/593 R

FOREIGN PATENTS OR APPLICATIONS 946,443   8/1956   Germany

Primary Examiner—James O. Thomas, Jr.
Assistant Examiner—James H. Reamer

[57] ABSTRACT

A process is provided for preparing methyl heptenone from mesityl oxide or acetone or mixtures thereof in improved yield.

Mesityl oxide is reacted with prenyl chloride to form a ketone mixture comprising mixed prenyl-substituted methyl pentenones, which is then separated from the residual reaction mixture by distillation, subjected to hydrolytic cracking with water in the presence of alkali at an elevated temperature, and methyl heptenone recovered.

The same ketone mixture is found as a by-product of the reaction of acetone with prenyl chloride in the presence of a catalyst to form methyl heptenone. This can therefore be subjected to the hydrolytic cracking reaction, thus increasing the amount of methyl heptenone produced.

35 Claims, No Drawings

PROCESS FOR PREPARING METHYL HEPTENONE

This application is a continuation-in-part of Ser. No. 484,494, filed July 8, 1974, and now abandoned.

In accordance with U.S. Pat. No. 3,668,255, patented June 6, 1972 to Meuly and Gradeff, a process is provided for the alkylation of aliphatic ketones having an alpha hydrogen, substitution occurring on the carbon alpha to the carbonyl group, by use of solid alkali in the presence of an organic amine and/or ammonia as a catalyst. The reaction products are alkenyl highly branched ketones having a pleasant odor, useful in the formulation of perfumes and perfume bases. Many of these ketones are prepared for the first time by this process.

The process is particularly useful for the preparation of methyl heptenone. If acetone is reacted with 1-chloro-3-methyl-2-butene, good yields of methyl heptenone are obtained. However, the methyl heptenone is accompanied by a higher boiling ketone fraction, that constitutes a considerable proportion of the reaction product. In Example 27 of the patent, for example, the yield included 86 grams of crude methyl heptenone and 42 grams of the higher ketone residue, and the crude methyl heptenone only comprised 72% methyl heptenone. Economic application of this process to the preparation of methyl heptenone clearly requires conversion of the higher boiling ketone fraction into a useful product.

Analysis of the higher boiling ketone fraction has shown that it is a mixture containing large amounts of isomeric ketones of the following structure:

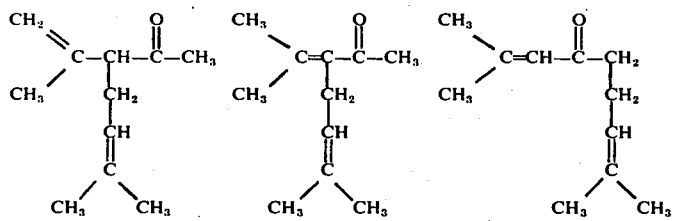

Acetone under the reaction conditions forms mesityl oxide, and this then reacts with the prenyl chloride to produce the above isomers; in the same manner, acetone reacts with prenyl chloride to produce methyl heptenone.

German Pat. No. 875,512 to Binapfl, ausgegeben May 4, 1953, proposed the hydrolysis of unsaturated ketones having a carbonyl group in the vicinity of an ethylenically unsaturated group by heating in the presence of water with the addition of acid, particularly weak acid, such as boric acid, adipic acid and benzoic acid. Rupture of the ketone molecule follows addition of water at the ethylenic linkage, and the product is a mixture of ketones and aldehydes. The process is indicated as applicable to aromatic and cycloaliphatic ketones, such as 1-cyclohexylidene-cyclohexanone-2 and 1-oxy-1,3-diphenyl-2-butylene.

German Pat. No. 927,688 to Stichnoth, ausgegeben May 16, 1955, suggested the conversion of o-cyclohexylidene-cyclohexanone to cyclohexanone, using water, in the presence of a small amount of alkali, at elevated temperatures.

German Pat. No. 946,443 to Wolf, published Feb. 2, 1956, proposed modification of the process of U.S. Pat. No. 875,512 by the use of alkali rather than acid. As the alkali, alkali metal hydroxides such as potassium and sodium hydroxide, as well as alkali metal compounds such as their carbonates, was suggested, as well as alkaline earth metal hydroxides such as calcium hydroxide. The process was indicated as applicable to cycloaliphatic and aromatic ketones, such as 1-cyclohexenyl-cyclohexanone-2- and acetophenone.

In accordance with the invention, it has now been determined that the higher boiling ketone mixture containing prenyl-substituted methyl pentenones can be converted to methyl heptenone and thus bolster the yield of methyl heptenone by hydrolytic cracking in the presence of alkali and water at a temperature within the range from about 50° to about 350° C. The resulting increased yield of methyl heptenone makes the production of methyl heptenone from acetone quite attractive commercially.

In accordance with the invention, a process is also provided for preparing methyl heptenone from mesityl oxide, which comprises reacting mesityl oxide at a temperature within the range from about −20° to about 150°C. with prenyl chloride in the presence of a solid alkali metal hydroxide selected from the group consisting of potassium hydroxide, sodium hydroxide, and mixtures thereof, and as a catalyst a nitrogen compound which is selected from the group consisting of ammonia, and aliphatic, cycloaliphatic, and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents, the amounts of the mesityl oxide and prenyl chloride being in the molar ratio of from about 1:5 to about 20:1, the alkali hydroxide being in the proportion of from about .1 to about 2 moles per mole of prenyl chloride, and the amount of nitrogen compound being within the range from about 0.003 mole to about 1 mole per mole of prenyl chloride; thereby forming and separating a prenyl-substituted methyl pentanone mixture; subjecting the ketone mixture to hydrolytic cracking with water in the presence of alkali at a temperature within the range from about 50° to about 350° C.; and recovering methyl heptenone from the resulting reaction mixture.

The process of the invention is applied to mesityl oxide is thus carried out in two steps with or without intermediate purification of the ketone mixture prior to hydrolytic cracking.

This reaction thus proceeds in accordance with the following reaction scheme:

Step 1
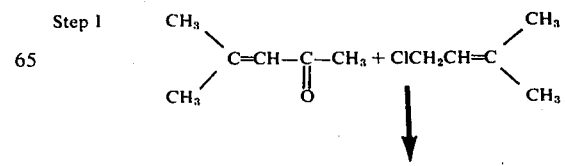

-continued

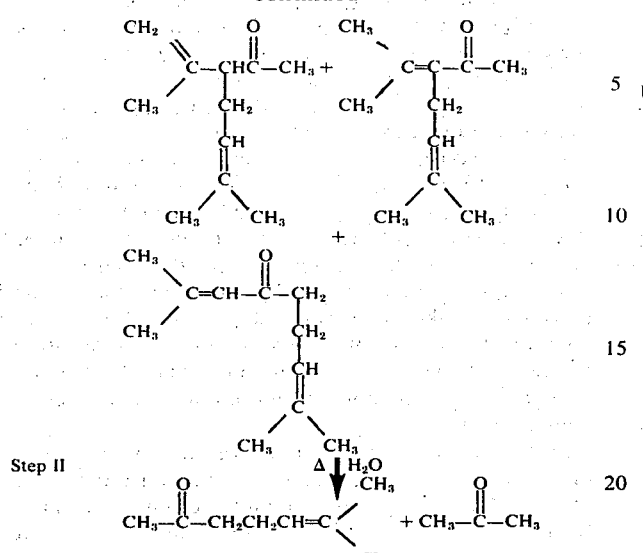

Step II

Further in accordance with the invention, a process is provided for preparing methyl heptenone from acetone, which comprises reacting acetone at a temperature within the range from about −20° to about 150°C. with prenyl chloride in the presence of a solid alkali metal hydroxide selected from the group consisting of potassium hydroxide, sodium hydroxide, and mixtures thereof, and as a catalyst a nitrogen compound which is selected from the group consisting of ammonia, and aliphatic, cycloaliphatic, and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents, the amounts of the acetone and prenyl chloride being in the molar ratio of from about 1:5 to about 20:1, the alkali hydroxide being in the proportion of from about 1 to about 2 moles per mole of prenyl chloride, and the amount of nitrogen compound being within the range from about 0.003 mole to about 1 mole per mole of prenyl chloride; recovering methyl heptenone from the reaction mixture, preferably by distillation; subjecting the residual ketonic mixture comprising prenyl-substituted methyl pentenones to hydrolytic cracking with water in the presence of alkali at a temperature within the range from about 50° to about 350° C.; and recovering additional methyl heptenone from the hydrolytic reaction mixture.

The process of the invention when starting with acetone is thus carried out in two steps, with separation of methyl heptenone produced in the first step before hydrolytic cracking of the prenyl-substituted methyl pentenones that are obtained as a by-product in the first step, in accordance with the following reaction scheme:

Step I
a).

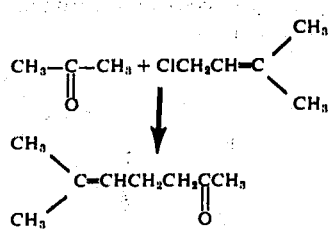

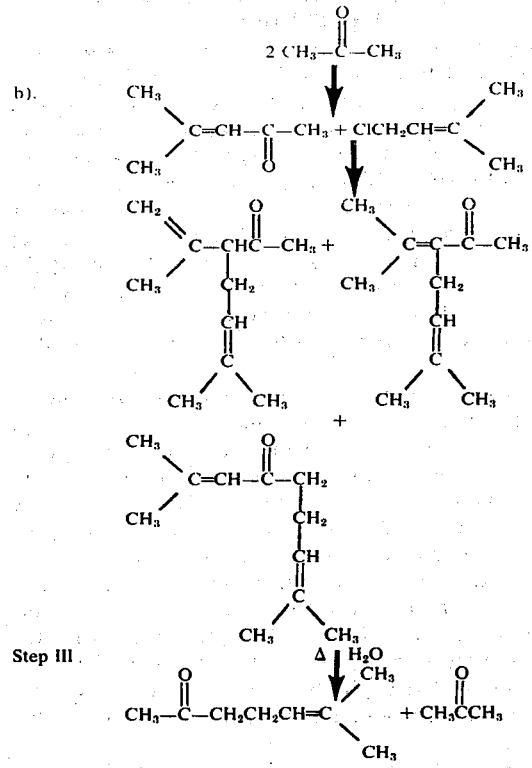

Step III

The reaction of Step I is a secondary one since the mesityl oxide is a by-product of the self-condensation of acetone that takes place under the reaction conditions.

Before carrying out Step II, the methyl heptenone produced in the reaction of Step I (a) must be separated from the products of the reaction of Step I (b).

The reaction between acetone or mesityl oxide and prenyl chloride is usually mildly exothermic, and the temperature of the reaction is not critical. The alkylation may be carried out over a wide temperature range, between about −20° and about 150° C. The alkylation proceeds at a satisfactory rate at room temperature, and more rapidly at elevated temperature, but it is not normally necessary to heat the reaction mixture at temperatures above from about 50° to about 100° C.

The reaction time may be as short as one hour, but if the reaction is kept at room temperature, 1 day or longer may be required.

It is preferable but not essential to have anhydrous conditions. Up to about 0.5 mole of water per mole of prenyl chloride can be present. Such water dissolves in the ketone.

The order of addition of the reactants is not critical, but very little reaction takes place until the catalyst is added. Thus, the reactants may be mixed together, or the prenyl chloride and solid alkali metal hydroxide can be added to the ketone and catalyst over a period of time, if a slow reaction is desired. Mixtures of sodium and potassium hydroxide can be used, but sodium hydroxide (which is less expensive) gives very satisfactory results.

It is important that the alkali metal hydroxide be in solid form, and it should also be paritculate. The particle size is not important. Reaction takes place even with coarsely-divided solid alkali metal hydroxides.

However, with aqueous or alcoholic sodium or potassium hydroxide solution yields are very low.

Auxiliary solvents or diluents are not necessary. Inert solvents such as petroleum ether, benzene and ethyl ether have no effect on the reaction. Hydroxylated solvents such as alcohols and glycols should not be used, because they may lead to hydrolysis of the prenyl chloride to the corresponding prenyl alcohol, and this will result in a loss of starting material, and consequently a lower yield.

Monoalkylation is favored by use of a molar ratio of ketone to prenyl chloride within the range from about 1:1 to about 20:1. The alkali metal hydroxide in this case is in the proportion between from about 1 to about 2 moles. The optimum proportion is about 1.1 to about 1.5 moles, based on the prenyl chloride.

The amount of nitrogen compound used as a catalyst can be as low as 0.003 mole, and amounts up to about 1 mole per mole of prenyl chloride can be used. The preferred amount is within the range from about 0.001 to about 0.1 mole.

The organic amine catalysts that have given good results are primary, secondary and tertiary amines having from one to about sixty carbon atoms, and are exemplified by the following: straight chain and branched chain saturated and unsaturated aliphatic amines and their salts, such as monomethylamine (anhydrous or in water solution); monomethylamine hydrochloride, glucosamine, mono-ethyl-, propyl-, butyl-, amyl-, -hexyl-, hexenyl-, heptyl-, -octyl-, -nonyl-, -decyl-, -dodecyl-, -oleyl- and -stearyl-amines; di-methyl-, -ethyl-, -propyl-, -allyl-, isopropyl-, -butyl-, -isobutyl-, -tert-butyl-, -benzyl-, -pentenyl-, -hexyl-, -heptyl-, -octyl-, -nonyl-, -dodecyl-, -stearyl-, -oleyl-, -behenyl-, and -myristyl- amines; tri-methyl-, -ethyl-, -propyl-, isopropyl-, -butyl-, -isobutyl-, sec-butyl-, -tert-butyl-, -amyl-, -isoamyl-, -tert-amyl-, -hexyl-, -isohexyl-, -isooctyl-, -dodecyl- -stearyl- and -oleyl- amines; mixed di and tri alkyl and alkenyl amines, the alkyl and alkenyl groups being selected from any of the above, such as dimethyl ethyl amine, diethyl butylamine, hexenyl dihexyl amine, diisopropyl butyl amine, diethyl propyl amine, methyl diisopropyl amine, dimethyl dodecylamine, benzyl dimethylamine; polyamines such as methylene diamine dihydrochloride, ethylene diamine, propylene diamine, and hexamethylene tetramine; ion-exchange resins, such as Amberlite IR-4B, Ionac A-260, and Ionac A-300, which contain aliphatic polyamine groups; saturated and unsaturated heterocyclic amines, exemplified by piperidine, pyrrole, piperazine, dimethyl glyoxime, methyl nitro imidazole, and morpholine; saturated and unsaturated cycloaliphatic amines, exemplified by cyclohexyl amine, cyclohexenyl amine, cyclopropyl amine, cyclopropenyl amine, and cycloheptyl amine; alkylolamines, exemplified by monoethanolamine, diethanolamine, and triethanolamine; hydrazine $NH_2-NH_2$; and amino acids, exemplified by glycine, taurine, and ethylene diamine tetraacetic acid. Also useful are amine derivatives that hydrolyze in the presence of sodium or potassium hydroxide to form an organic amine having from one to about eighteen carbon atoms, such as organic amides, for example dimethyl formamide, dimethyl acetamide, sulfanilamide, diamyl acetamide; and substituted ureas such as dimethyl urea. Also useful are labile quaternary amines that generate the corresponding amine in the presence of base.

Also effective are ammonia and inorganic ammonium salts that are hydrolyzed to form ammonia in the presence of sodium or potassium hydroxide, such as ammonium chloride, ammonium bromide, ammonium nitrate, ammonium carbonate, ammonium sulfate, ammonium phosphate, and ammonium ferric oxalate, ammonium cobalt sulfate and hydroxyl amine hydrochloride.

The course of the reaction can be conveniently followed by the decrease in the content of prenyl chloride. The reaction mixture at the conclusion of the reaction is worked up by filtering off the solid halide salt and the excess of alkali metal hydroxide, or by dissolving them in water. The desired methyl heptenone and higher boiling ketone fraction can then be isolated from the organic layer by distillation, such as by steam distillation or by fractional distillation, in conventional manner.

The first materials recovered in distillation are of course the lower boiling materials, so that first any residual acetone or mesityl oxide and prenyl chloride are distilled off, followed by any methyl heptenone. After any methyl heptenone fraction has been removed, the higher boiling ketone fraction starts to come over. The desired higher boiling ketone fraction has a boiling range from about 54° to about 121° C. at between 0.2 and 1 mm Hg. This mixture is recovered and subjected to hydrolytic cracking in accordance with the invention in order to obtain methyl heptenone.

To prepare the prenyl substituted methyl pentenones or ketone mixture comprising prenyl-substituted methyl pentenones for hydrolytic cracking, the ketones are combined with water. For complete conversion of the ketones, the amount of water should be at least the stoichiometric amount, one mole per mole of prenyl-substituted methyl pentenones, but a considerable excess of water can be used, and may even be beneficial. There is no critical upper limit on the amount of water, except as large amounts impose handling difficulties. In many cases, it has been noted that amounts within the range from about 0.5 part to about 5 parts per part of prenyl-substituted methyl pentenones give excellent yields that are improved as compared to like runs with less water, even though such lesser amounts are more than the required mole-per-mole ratio. Evidently, excess water has a solvent or solvating function or some unknown chemical or physical function favorably influencing the reaction.

Alkali hydroxide or other alkaline compound is employed in the molar proportion within the range from about 0.001 to about 0.5 per mole of ketone. Preferably, the amount is within the range from about 0.01 to about 0.08.

As the alkali hydroxide there can be used any alkali metal hydroxide, such as sodium hydroxide, and potassium hydroxide, as well as alkaline earth metal hydroxides, such as calcium hydroxide, strontium hydroxide and barium hydroxide. Also useful are alkaline-reacting salts such as the alkali metal and alkaline earth metal carbonates, borates, tartrates, oxalates, acetates, formates and sulfites, for example, sodium carbonate and potassium carbonate.

The hydrolytic cracking is carried out at elevated temperatures, and can be carried out under pressure or in a pressure vessel. The reaction may be conducted over a wide temperature range within the range from about 50° to about 350°C., and preferably within the range from about 230° to about 310°C.

The reaction will proceed at atmospheric pressure. However, in order to retain volatile ingredients in the reaction system at elevated temperatures, the reaction can be carried out under a condenser, or in a pressure vessel such as an autoclave. In the latter case, high pressures may develop in the vessel without disadvantage, up to and including 1000 psi.

The reaction time depends to some extent upon the reaction temperature, and the strength of the alkali catalyst used. In many instances, the reaction is complete within a matter of 15 to 20 minutes, but in some cases a longer time may be required, up to one day or longer.

Addition of acetone or other low boiling aliphatic ketone otherwise stable under the reaction conditions increases the reaction rate considerably, and permits completion of the cracking in a very short time, ranging from about one minute to about one hour. The aliphatic ketones useful for this purpose contain from about three to about ten carbon atoms, in a straight or branched chain.

The same effect on the reaction rate is exerted by lower aliphatic alcohols such as methanol, ethanol, isopropanol, butanol, isobutanol, amyl and isoamyl alcohol, as well as prenyl alcohol.

The reaction product is composed of a mixture of acetone, methyl heptenone, and possibly other ketones, depending upon the starting material. From this reaction mixture the methyl heptenone is easily separated, usually by fractional distillation.

In the process of preparing methyl heptenone from acetone, part of the mesityl oxide that is formed as a by-product reacts with the prenyl chloride, while the rest is recovered with the excess of acetone.

In accordance with this invention separation of the acetone and mesityl oxide is not necessary. In fact, it is advantageous to react a mixture of acetone and mesityl oxide with prenyl chloride, since the prenyl mesityl oxide that might be formed will be converted in very high yield to methyl heptenone by the hydrolytic cracking reaction. This is an important improvement in the process of U.S. Pat. No. 3,668,255 that ads convenience and flexibility to an improved yield of methyl heptenone.

The following Examples in the opinion of the inventors represent preferred embodiments of the invention:

EXAMPLE 1 a. Preparation of Prenyl Mesityl Oxide (PMO)

To a well stirred mixture of 60 g of 96% sodium hydroxide and 600 g of mesityl oxide was added 3 g of diethylamine, followed by 105 g of 94% 1-chloro-3-methyl-2-butene. The mixture was then heated to 70° C. over a 10 minute period, and the external heat source immediately removed. The mass continued to rise in temperature to 80° C. over a 10 minute period, and was then maintained at between 79° and 82° C. over a 2.3 hour period, with either heating or cooling, as needed. After cooling to 30° C., the mixture was quenched with 250 ml of water and stirred vigorously. The organic phase was then separated and the aqueous layer extracted four times with 20 ml portions of benzene. The organic phases were combined and dried overnight over sodium sulfate. The dried oil phase was then treated with 2 ml of acetic acid prior to distillation. The yield was 123.7 g of the mixture of prenyl mesityl oxide isomers.

| TIME (HR.) | VACUUM (mm Hg) | KETTLE TEMP. °C. | VAPOR TEMP. °C. | WEIGHT (g) | COMMENTS |
|---|---|---|---|---|---|
| 0 | 760 | 29 | 29 | | |
| 1 | 760 | 110 | 84 | 77.4 | Vacuum gradually increased |
| 7.6 | 760 – 98 | 110 – 92 | 90 – 76 | 447.4 | Contains 0.8% PMO* |
| 4.6 | 98 – 2 | 96 – 164 | 58 – 145 | 276.6 | Contains 47.3% PMO* |

*Mixture of isomers of prenyl mesityl oxide.

b. Hydrolytic Cleavage of Prenyl Mesityl Oxide (PMO) from (a)

Into a 1-liter stainless steel autoclave equipped with a high speed turbine type agitator were changed:

Prenyl mesityl oxide 166 g at 89% purity
Water 358 g
Sodium Hydroxide 1.7 g
Acetone 30 g Samples were taken during the reaction and analyzed by vapor gas chromatography for prenyl mesityl oxide (PMO) and methyl heptenone (MH). The reaction log was as follows:

| TIME | TOTAL MINUTES | TEMP. °C. | PRESSURE PSI | SAMPLE # | PMP | MH | % REACTION |
|---|---|---|---|---|---|---|---|
| 8:30 | 0.0 | 25 | — | — | 89.1 | — | — |
| 9:10 | 40.0 | 140 | 220 | 1 | 80.0 | 4.6 | 5.1 |
| 9:20 | 50.0 | 185 | 340 | 2 | 75.7 | 10.9 | 12.6 |
| 9:30 | 60.0 | 230 | 900 | 3 | 0 | 73.8 | 100 |

After cooling, the autoclave was discharged, rinsed with acetone and the two layers separated after salting the organic layer with 30 g NaCl. The aqueous layer was then extracted with benzene. The combined organic layer and benzene extracts were distilled at 28 mm vacuum after removal of the benzene. Analysis of all fractions indicated a total of 98.7 g methyl heptenone recovered. The amount of the residue was 4.3 g. According for 0.078 mole PMO taken out of the reaction mixture during the reaction for sampling, the yield amounted to 95.5% of theory.

EXAMPLE 2 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a 1-liter stainless steel autoclave equipped with a high speed turbine type agitator were charged:

Prenyl mesityl oxide 166 g at 89.5% purity
    Water 250 g
    Sodium hydroxide 1.7 g
    Acetone 30 g The reaction was carried out as in Example 1 (b), to a maximum temperature of 230° C. and a maximum pressure of 880 psi for 1 hour.

After cooling, the autoclave was discharged, rinsed with acetone and the two layers separated after salting the organic layer with 30 g NaCl. The aqueous layer was then extracted with benzene. The combined organic layer and benzene extracts were distilled at 28 mm vacuum after removal of the benzene. Analysis of all fractions indicated a total of 98.7 g methyl heptenone recovered. Accounting for 0.078 mole PMO taken out of the reaction mixture during the reaction for sampling, the yield amounted to 95.1% of theory.

EXAMPLE 3 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

In to a 1-liter stainless steel autoclave equipped with a high speed turbine type agitator were charged:

Prenyl mesityl oxide 165 g at 89.5% purity
    Water 350 g
    Sodium Hydroxide 1.7 g The reaction was carried out as in Example 1 (b) to a maximum temperature of 230° C. and a maximum pressure of 720 psi for 1 hour.

After cooling, the autoclave was discharged, rinsed with acetone and the two layers separated after salting the organic layer with 30 g NaCl. The aqueous layer was then extracted with benzene. The combined organic layer and benzene extracts were distilled at 28 mm vacuum after removal of the benzene. Analysis of all fractions indicated a total of 74.1 g methyl heptenone recovered. Accounting for 0.078 mole PMO taken out of the reaction mixture during the reaction for sampling, the yield amounted to 74% of theory.

EXAMPLE 4 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a one-liter stainless steel autoclave equipped with a high speed turbine agitator were charged:

Prenyl mesityl oxide 184 g at 99.5% purity
    Water 400 g
    Sodium Hydroxide 1.8 g The reaction was carried out as in Example 1 (b) for 1 hour to a maximum temperature of 230° F. and a maximum pressure of 520 psi.

After cooling, the autoclave was discharged, rinsed with acetone and the two layers separated after salting the organic layer with 30 g NaCl. The aqueous layer was then extracted with benzene. The combined organic layer and benzene extracts were distilled at 28 mm vacuum after removal of the benzene. Analysis of all fractions indicated a total of 80.4 g methyl heptenone recovered. Accounting for 0.078 mole PMO taken out of the reaction mixture during the reaction for sampling, the yield amounted to 60% of theory.

EXAMPLE 5 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a 1-liter stainless steel autoclave equipped with a high speed turbine type agitator were charged:

Prenyl mesityl oxide 165 g at 89.5% purity
    Water 100 g
    Sodium Hydroxide 1.7 g
    Acetone 30 g The reaction was carried out as in Example 1 (b) for 1 hour to a maximum temperature of 230° C. and a maximum pressure of 800 psi.

After cooling, the autoclave was discharged, rinsed with acetone and the two layers separated after salting the organic layer with 30 g NaCl. The aqueous layer was then extracted with benzene. The combined organic layer and benzene extracts were distilled at 28 mm vacuum after removal of the benzene. Analysis of all fractions indicated a total of 72.2 g methyl heptenone recovered. Accounting for 0.078 mole PMO taken out of the reaction mixture during the reaction for sampling, the yield amounted to 72% of theory.

EXAMPLE 6 a. Preparation of Prenyl Mesityl Oxide from Acetone

To a well-stirred mixture of 1 mole (110 parts) of 95 percent 1-chloro-3-methyl-2-butene and 5 moles (290 parts) of acetone, were added 0.10 mole (8.6 parts) of piperidine and 1.5 moles (63 parts) of 96 percent caustic soda flakes. After keeping the temperature at 30° to 35° C. for 1 hour, titration indicated that 67 percent of 1-chloro-3-methyl-2-butene had reacted. This titration was conducted by adding to a measured sample of the reaction mixture an excess of 50 percent alcoholic potassium hydroxide, which, on heating, hydrolyzed the chloride to the carbinol, with liberation of hydrochloric acid. The latter was neutralized by the potassium hydroxide, and the excess alcoholic alkali titrated.

After 3 hours, when the unreacted 1-chloro-3-methyl-2-butene had dropped to 5 percent of the original, the reaction mass was cooled to 20° C., filtered to remove sodium chloride and the excess caustic soda, and the liquid phase distilled. There was obtained 86 parts of crude methyl heptenone (b.p. 55° – 85° C./13 mm.) and 42 parts of a higher boiling residue. The curde methylheptenone analyzed 72 percent methyl heptenone by V.P.C., corresponding to a yield of 49 percent methyl heptenone from the 1-chloro-3-methyl-2-butene. Fractional distillation of the crude methyl heptenone yielded 46 parts of pure methyl heptenone, purity 98 – 100 percent by V.P.C., b.p. 170° C./760 mm; $n_D^{20}$ = 1.4410.

The reported refractive index of pure 6-methyl-5-hepten-2-one is $n_D^{20}$ = 1.4410 – 1.4415, Bull Soc. Chim. France [4] 39 1125 (1926).

The 42 parts of higher boiling fraction contained 30.7% prenyl mesityl oxide and 2.8 parts methyl heptenone.

b. Hydrolytic Cleavage of Prenyl mesityl Oxide (PMO) from (a)

Into a 1-liter stainless steel autoclave equipped with a high speed turbine type agitator were charged:

Prenyl mesityl oxide 184 g at 30.7% purity
containing 2.8% methyl heptenone
Water 400 g
Sodium Hydroxide 1.8 g The reaction was carried out as in Example 1 (b) for 4.5 hours to a maximum temperature of 230° C. and a maximum pressure of 520 psi.

After cooling, the autoclave was discharged, rinsed with acetone and the two layers separated after salting the organic layer with 30 g NaCl. The aqueous layer was then extracted with benzene. The combined organic layer and benzene extracts were distilled at 28 mm vacuum after removal of the benzene. Analysis of all fractions indicated a total of 36.0 g methyl heptenone recovered. Accounting for 0.078 mole PMO taken out of the reaction mixture during the reaction for sampling, the yield amounted to 84.2% of theory.

EXAMPLE 7 a. Preparation of Prenyl Mesityl Oxide From Acetone

A higher boiling prenyl mesityl oxide fraction containing 14.3% prenyl mesityl oxide was prepared from acetone as in Example 6 (a).

b. Hydrolytic Cleavage of Prenyl Mesityl Oxide (PMO) from (a)

Into a 1-liter stainless steel autoclave equipped with a high speed turbine type agitator were charged:

Prenyl mesityl oxide 165 g at 14.3% purity
containing 1.2 g methyl heptenone
Water 350 g
Sodium Hydroxide 1.7 g
Isopropanol 184 g The reaction was carried out as in Example 1 (b) for 1.3 hours to a maximum temperature of 230° C. and a maximum pressure of 800 psi.

After cooling, the autoclave was discharged, rinsed with acetone and the two layers separated after salting the organic layer with 30 g NaCl. The aqueous layer was then extracted with benzene. The combined organic layer and benzene extracts were distilled at 28 mm vacuum after removal of the benzene. Analysis of all fractions indicated a total of 17.2 g methyl heptenone recovered. Accounting for 0.078 mole PMO taken out of the reaction mixture during the reaction for sampling, the yield amounted to 95.8% of theory.

EXAMPLE 8 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a 1-liter stainless steel autoclave equipped with a high speed turbine type agitator were charged:

Prenyl mesityl oxide 35 g
Water and sodium carbonate
as 1% aqueous sodium carbonate 43 g Samples were taken during the reaction, and analyzed by vapor phase chromatography for prenyl mesityl oxide (PMO) and methyl heptenone (MH). The reaction log was as follows:

| TIME TOTAL MINUTES | TEMP °C | PRESSURE PSI | SAMPLE | PMO | MH | % REACTION |
|---|---|---|---|---|---|---|
| 0 | 30 | 0 | 1 | 94.6 | 0 | 0 |
| 30 | 237 | 60 | | | | |
| 60 | 275 | 425 | | | | |
| 90 | 275 | 500 | 2 | 87.5 | 7.2 | 7.6 |
| 120 | 275 | 530 | | | | |

A total of 29.4 g organic material was recovered. Analysis indicated 9.16 g methyl heptenone (0.0726 mole). Taking into account 28.06 g (0.1688 mole) of prenyl mesityl oxide recovered, the direct yield was 28.59%, and the true yield 85.4%.

EXAMPLE 9 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a 1-liter stainless steel autoclave equipped with a high speed turbine type agitator were charged:

Prenyl mesityl oxide 40.3 g
Water and potassium hydroxide
as 0.1% aqueous potassium hydroxide 51.4 g Samples were taken during the reaction and analyzed by vapor phase chromatography for prenyl mesityl oxide (PMO) and methyl heptenone (MH). The reaction log was as follows:

| TIME TOTAL MINUTES | TEMP °C | PRESSURE PSI | SAMPLE | PMO | MH | % REACTION |
|---|---|---|---|---|---|---|
| 0 | 35 | 0 | 1 | 94.6 | 0 | 0 |
| 30 | 230 | 80 | | | | |
| 60 | 275 | 475 | | | | |
| 90 | 275 | 545 | 2 | 60.3 | 28.2 | 31.9 |
| 120 | 275 | 590 | | | | |

The total organic fraction recovered was 34.8 g. Analysis indicated 15.1 g methyl heptenone (0.119 mole). Taking into account 0.089 mole PMO recovered, the direct yield was 60.5% and the true yield 90.2%.

EXAMPLE 10 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a 1-liter stainless steel autoclave equipped with a high speed turbine type agitator were charged:

| | |
|---|---|
| Prenyl mesityl oxide | 40.0 g |
| Water and tetramethyl ammonium hydroxide as a 1% aqueous tetramethyl ammonium hydroxide solution | 50.0 g |

The reaction was carried out as set forth in the reaction log below. Samples were taken during the reaction, and analyzed by vapor phase chromatography for prenyl mesityl oxide PMO and methyl heptenone (MH). The reaction log was as follows:

| TIME TOTAL MINUTES | TEMP °C | PRESSURE PSI | SAMPLE | PMO | MH | % REACTION |
|---|---|---|---|---|---|---|
| 0 | 83 | 0 | 1 | 94.6 | 0 | 0 |
| 30 | 235 | 80 | | | | |
| 60 | 275 | 400 | | | | |
| 94 | 275 | 475 | 2 | 93.5 | 1.2 | 1.3 |
| 120 | 275 | 475 | | | | |

A total of 36.1 g organics was recovered. Analysis indicated 2 g (0.0150 mole) methyl heptenone. Taking into account 0.180 mole PMO recovered, the direct yield was 7.9% and the true yield 91.3%.

EXAMPLE 11 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a 1-liter stainless steel autoclave equipped with a high speed turbine type agitator were charged:

| | |
|---|---|
| Prenyl mesityl oxide | 50.5 g |
| Water and dimethylamine as 0.4% aqueous dimethylamine | 43 g |

Samples were taken during the reaction and analyzed by vapor phase chromatography for prenyl mesityl oxide (PMO) and methyl heptenone (MH). The reaction log was as follows:

| TIME TOTAL MINUTES | TEMP °C | PRESSURE PSI | SAMPLE II | PMO | MH | % REACTION |
|---|---|---|---|---|---|---|
| 0 | 35 | 0 | 1 | 94.6 | 0 | 0 |
| 30 | 215 | 70 | | | | |
| 60 | 275 | 510 | | | | |
| 90 | 275 | 520 | 2 | 93.5 | 1.0 | 1.0 |
| 120 | 275 | 525 | | | | |

A total of 33.7 g organics was recovered. Analysis indicated 1.85 g methyl heptenone (0.015 mole). The direct yield was 7.3 % and the true yield 37%.

EXAMPLE 12 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a 1-liter stainless steel autoclave equipped with a high speed turbine type agitator were charged:

| | |
|---|---|
| Prenyl mesityl oxide | 100 g |
| Water and hexadecyl trimethyl ammonium bromide as 1% aqueous hexadecyl trimethyl ammonium bromide | 50 g |

Samples were taken during the reaction and analyzed by vapor phase chromatography for prenyl mesityl oxide (PMO) and methyl heptenone (MH). The reaction log was as follows:

| TIME TOTAL MINUTES | TEMP °C | PRESSURE PSI | SAMPLE | PMO | MH | % REACTION |
|---|---|---|---|---|---|---|
| 0 | 35 | 0 | 1 | 94.6 | 0 | 0 |
| 30 | 250 | 160 | | | | |
| 60 | 275 | 470 | | | | |
| 90 | 275 | 625 | 2 | 94.0 | 0.4 | 0.4 |

A total of 34.9 g organics was recovered. Analysis indicated 1.33 g methyl heptenone (0.0105 mole). The direct yield was 5.2% and the true yield 55.7%.

EXAMPLE 13 a. Preparation of Prenyl Mesityl Oxide (PMO)

A mixture of prenyl mesityl oxide isomers was prepared as in Example 1 (a).

b. Hydrolytic Cleavage of Prenyl Mesityl Oxide (PMO) from (a)

Into a 1-liter stainless steel reaction vessel equipped with a distillation line and vapor recovery condenser were charged:

| | |
|---|---|
| Prenyl mesityl oxide | 100 g |
| Water and sodium hydroxide as 30% aqueous sodium hydroxide | 140 g |

The reaction was carried out at 140°C at atmospheric pressure, distilling off acetone as it was formed. Samples were taken during the reaction, and analyzed by vapor phase chromatography for prenyl mesityl oxide (PMO) and methyl heptenone (MH). The reaction log was as follows:

| TIME TOTAL MINUTES | TEMP °C | SAMPLE | PMO | MH |
|---|---|---|---|---|
| 0 | 30 | | | |
| 240 | 90 | 1 | 92.5 | 0 |
| 480 | 140 | 2 | 81.6 | 7.4 |
| 720 | 140 | 3 | 70.2 | 13.3 |
| 960 | 140 | 4 | 60.0 | 18.2 |

After cooling, the reaction vessel was discharged, rinsed with acetone and the two layers separated after salting the organic layer with 50.0 g sodium chloride. The aqueous layer was then extracted with benzene. The combined organic layer and benzene extracts were distilled at 28mm vacuum after removal of the benzene.

A total of 97 g organics was recovered. Analysis of the combined fractions indicated 15.0 g methyl heptenone (0.126 mole). The direct yield was 20.0% and the true yield 50.0%.

Having regard to the foregoing disclosure, the following is claimed as the inventive and patentable embodiments thereof:

1. In the process for preparing methyl heptenone from acetone which comprises reacting acetone at a temperature within the range from about −20° to about 150°C. with prenyl chloride in the presence of solid alkali metal hydroxide selected from the group consisting of potassium hydroxide, sodium hydroxide, and mixtures thereof, and as a catalyst a nitrogen compound which is selected from the group consisting of ammonia and aliphatic, cycloaliphatic and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro-substituents; the amounts of the acetone and prenyl chloride being in the molar ratio of from about 1:5 to about 20:1; the alkali metal hydroxide being in the proportion of from about 1 to about 2 moles per mole of prenyl chloride, and the amount of nitrogen compound being within the range from about 0.003 mole to about 1 mole per mole of prenyl chloride, the improvement which comprises separating methyl heptenone from the reaction mixture comprising prenyl-substituted methyl pentenones; subjecting the prenyl substituted methyl pentenones to hydrolytic cracking with water in the presence of alkali selected from the group consisting of alkali metal and alkaline earth metal hydroxides at a temperature within the range from about 50° to about 350°C., and recovering additional methyl heptenone from the resulting reaction mixture, thereby improving the overall yield of methyl heptenone from acetone.

2. A process according to claim 1, in which the amount of alkali in the hydrolytic cracking reaction is within the range from about 0.001 to about 0.5 mole per mole of ketone.

3. A process according to claim 1, in which the amount of alkali is within the range from about 0.01 to about 0.08 mole per mole of ketone.

4. A process according to claim 1, in which the amount of water in the hydrolytic cracking reaction is at least one mole per mole of ketone.

5. A process according to claim 1, in which the amount of water in the hydrolytic cracking reaction is within the range from about 0.5 part to about 5 parts per part of ketone.

6. A process in accordance with claim 1, in which the hydrolytic cracking is carried out at a temperature within the range from about 230° to about 310° C.

7. A process in accordance with claim 1, in which the alkali is an alkali metal or alkaline earth metal hydroxide.

8. A process in accordance with claim 1, in which the hydrolysis is carried out under a superatmospheric pressure up to about 1000 psi.

9. A process in accordance with claim 1, in which a prenyl substituted methyl pentenone fraction is separated from the methyl heptenone reaction mixture and subjected to hydrolytic cracking without further purification.

10. A process in accordance with claim 1, in which the hydrolytic cracking is carried out in the presence of a low boiling aliphatic ketone having from three to about ten carbon atoms.

11. A process in accordance with claim 1, in which the hydrolytic cracking is carried out in the presence of a lower aliphatic alcohol having from one to about five carbon atoms.

12. A process in accordance with claim 1 in which a mixture of mesityl oxide and acetone is reacted with the prenyl chloride.

13. In the process for preparing methyl heptenone from mesityl oxide which comprises reacting mesityl oxide at a temperature within the range from about −20° to about 150°C with prenyl chloride in the presence of solid alkali metal hydroxide selected from the group consisting of potassium hydroxide, sodium hydroxide, and mixtures thereof, and as a catalyst a nitrogen compound which is selected from the group consisting of ammonia and aliphatic, cycloaliphatic and heterocyclic hydrocarbon amines having from one to about sixty carbon atoms, such hydrocarbon amines containing hydroxy substituents, such hydrocarbon amines containing carboxylic acid substituents, and such hydrocarbon amines containing nitro substituents; the amounts of the mesityl oxide and prenyl chloride being in the molar ratio of from about 1:5 to about 20:1, the alkali metal hydroxide being in the proportion of from about 1 to about 2 moles per mole of prenyl chloride, and the amount of nitrogen compound being within the range from about 0.003 mole to about 1 mole per mole of prenyl chloride; the improvement which comprises separating from the reaction mixture a fraction comprising prenyl-substituted methyl pentenones; subjecting the prenyl-substituted methyl pentenone fraction to hydrolytic cracking with water in the presence of alkali selected from the group consisting of alkali metal and alkaline earth metal hydroxides at a temperature within the range from about 50° to about 350°C.; and recovering methyl heptenone from the resulting reaction mixture, thereby improving the overall yield of methyl heptenone from mesityl oxide.

14. A process according to claim 13, in which the amount of alkali in the hydrolytic cracking reaction is within the range from about 0.001 to about 0.5 mole per mole of ketone.

15. A process according to claim 13, in which the amount of alkali is within the range from about 0.01 to about 0.08 mole per mole of ketone.

16. A process according to claim 13, in which the amount of water in the hydrolytic cracking reaction is at least 1 mole per mole of ketone.

17. A process according to claim 13, in which the amount of water in the hydrolytic cracking reaction is within the range from about 0.5 part to about 5 parts per part of ketone.

18. A process in accordance with claim 13, in which the hydrolytic cracking is carried out at a temperature within the range from about 230° to about 310° C.

19. A process in accordance with claim 13, in which the alkali is an alkali metal or alkaline earth metal hydroxide.

20. A process in accordance with claim 13, in which the hydrolysis is carried out under a superatmospheric pressure up to about 1000 psi.

21. A process in accordance with claim 13 in which the prenyl-substituted methyl pentenone fraction is separated from the reaction mixture and subjected to hydrolytic cracking without further purification.

22. A process in accordance with claim 13, in which the hydrolytic cracking is carried out in the presence of a low boiling aliphatic ketone having from three to about ten carbon atoms.

23. A process in accordance with claim 13, in which the hydrolytic cracking is carried out in the presence of a lower aliphatic alcohol having from one to about five carbon atoms.

24. A process for preparing methyl heptenone from a mixture comprising prenyl-substituted methyl pentenones which comprises subjecting the prenyl-substituted methyl pentenone mixture to hydrolytic cracking with water in the presence of alkali selected from the group consisting of alkali metal and alkaline earth metal hydroxides at a temperature within the range from about 50° to about 350°C.; and recovering methyl heptenone from the resulting reaction mixture.

25. A process according to claim 24, in which the amount of alkali in the hydrolytic cracking reaction is within the range from about 0.001 to about 0.5 mole per mole of ketone.

26. A process according to claim 24, in which the amount of water in the hydrolytic cracking reaction is at least one mole per mole of ketone.

27. A process according to claim 24, in which the amount of water in the hydrolytic cracking reaction is within the range from about 0.5 part to about 5 parts per part of ketone.

28. A process according to claim 24, in which the amount of alkali is within the range from about 0.01 to about 0.08 mole per mole of ketone.

29. A process in accordance with claim 24 in which the hydrolytic cracking is carried out at a temperature within the range from about 230° to about 310° C.

30. A process in accordance with claim 24, in which the alkali is an alkali metal or alkaline earth metal hydroxide.

31. A process in accordance with claim 24, in which the hydrolysis is carried out under a superatmospheric pressure up to about 1000 psi.

32. A process in accordance with claim 24, in which the hydrolytic cracking is carried out in the presence of a low boiling aliphatic ketone having from three to about ten carbon atoms.

33. A process in accordance with claim 24, in which the hydrolytic cracking is carried out in the presence of a lower aliphatic alcohol having from one to about five carbon atoms.

34. A process in accordance with claim 24, in which the ketone mixture is obtained by reaction of mesityl oxide and prenyl chloride.

35. A process in accordance with claim 24, in which the ketone mixture is obtained by reaction of acetone and prenyl chloride.

* * * * *